US011802877B2

(12) United States Patent
Aghvanyan et al.

(10) Patent No.: US 11,802,877 B2
(45) Date of Patent: Oct. 31, 2023

(54) LUNG CANCER BIOMARKERS

(71) Applicant: Meso Scale Technologies, LLC., Rockville, MD (US)

(72) Inventors: Anahit Aghvanyan, Gaithersburg, MD (US); Eli N. Glezer, Del Mar, CA (US); John Kenten, Boyds, MD (US); Sudeep Kumar, Hackettstown, NJ (US); Galina Nikolenko, Germantown, MD (US); Martin Stengelin, Gaithersburg, MD (US); Srikant Vaithilingam, Baltimore, MD (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 296 days.

(21) Appl. No.: 16/883,468

(22) Filed: May 26, 2020

(65) Prior Publication Data
US 2021/0116452 A1  Apr. 22, 2021

Related U.S. Application Data

(60) Continuation of application No. 15/813,418, filed on Nov. 15, 2017, now abandoned, which is a division of application No. 14/447,691, filed on Jul. 31, 2014, now abandoned.

(60) Provisional application No. 61/945,006, filed on Feb. 26, 2014, provisional application No. 61/860,958, filed on Aug. 1, 2013.

(51) Int. Cl.
*G01N 33/574* (2006.01)

(52) U.S. Cl.
CPC ... *G01N 33/57423* (2013.01); *G01N 2800/52* (2013.01)

(58) Field of Classification Search
CPC .............. G01N 2800/52; G01N 33/57423
See application file for complete search history.

(56) References Cited

U.S. PATENT DOCUMENTS

| | | | |
|---|---|---|---|
| 4,168,146 A | 9/1979 | Grubb et al. | |
| 4,235,601 A | 11/1980 | Deutsch et al. | |
| 4,366,241 A | 12/1982 | Tom et al. | |
| 4,442,204 A | 4/1984 | Greenquist et al. | |
| 5,208,535 A | 5/1993 | Nakayama et al. | |
| 5,807,522 A | 9/1998 | Brown et al. | |
| 6,110,426 A | 8/2000 | Shalon et al. | |
| 7,497,997 B2 | 3/2009 | Glezer et al. | |
| 7,842,246 B2 | 11/2010 | Wohlstadter et al. | |
| 7,981,362 B2 | 7/2011 | Glezer et al. | |
| 8,790,578 B2 | 7/2014 | Wohlstadter et al. | |
| 8,808,627 B2 | 8/2014 | Wohlstadter et al. | |
| 2003/0113713 A1 | 6/2003 | Glezer et al. | |
| 2003/0207290 A1 | 11/2003 | Kenten et al. | |
| 2004/0022677 A1 | 2/2004 | Wohlstadter et al. | |
| 2004/0189311 A1 | 9/2004 | Glezer et al. | |
| 2005/0052646 A1 | 3/2005 | Wohlstadter et al. | |
| 2005/0142033 A1 | 6/2005 | Glezer et al. | |
| 2006/0105419 A1 | 5/2006 | Blankenberg et al. | |
| 2006/0205012 A1 | 9/2006 | Debad et al. | |
| 2007/0178504 A1 | 8/2007 | Colpitts et al. | |
| 2009/0075299 A1* | 3/2009 | Mathew ........... | G01N 33/57449 435/7.1 |
| 2010/0070191 A1 | 3/2010 | Gold et al. | |
| 2011/0152345 A1* | 6/2011 | Nakamura ............. | C07K 16/22 435/6.19 |
| 2014/0220006 A1 | 8/2014 | Aghvanyan et al. | |
| 2014/0329721 A1 | 11/2014 | Joern et al. | |
| 2015/0038365 A1 | 2/2015 | Aghvanyan et al. | |
| 2017/0160281 A1 | 6/2017 | Aghvanyan et al. | |
| 2018/0074061 A1 | 3/2018 | Aghvanyan et al. | |
| 2020/0158731 A1* | 5/2020 | Aghvanyan ...... | G01N 33/57423 |

FOREIGN PATENT DOCUMENTS

| WO | 99/26067 A1 | 5/1999 |
|---|---|---|
| WO | 2004/058055 A2 | 7/2004 |

OTHER PUBLICATIONS

Berns A., "Gene Expression in Diagnosis", Cancer 403:491-492 (2000).
Chakravarty P.K. et al., "Flt3-Ligand Administration After Radiation Therapy Prolongs Survival in a Murine Model of Metastatic Lung Cancer", Cancer Research 59(24):6028-6032 (Dec. 15, 1999).
Chen R. et al., "Simultaneous Quantification of Six Human Cytokines in a Single Sample Using Microparticle-Based Flow Cytometric Technology", Clinical Chemistry 45(9):1693-1694 (1999).
Delehanty J.B., "Printing Functional Protein Microarrays Using Piezoelectric Capillaries", Methods in Molecular Biology 264:135-143 (2004).
Gao S P. et al., "Mutations in the EGFR Kinase Domain Mediate STAT3 Activation Via IL-6 Production in Human Lung Adenocarcinomas", The Journal of Clinical Investigation 117(12):3846-3856 (Dec. 2007).
Ladanyi M. et al., "Lung Adenocarcinoma: Guiding EGFR-Targeted Therapy and Beyond", Modern Pathology 21:S16-S22 (2008).
Lim B J et al., "Expression of Metastasis-Associated Molecules in Non-Small Cell Lung Cancer and Their Prognostic Significance", Molecular Medicine Reports 3:43-49 (2010).
Lovett R.A., "Toxicogenomics: Toxicologists Brace for Genomics Revolution", Science 289(5479):536-537 (2000).
Lue R.Y.P. et al., "Site-Specific Immobilization of Biotinylated Proteins for Protein Microarray Analysis", Methods in Molecular Biology 264:85-100 (2004).
Park M.K. et al., "A Latex Bead-Based Flow Cytometric Immunoassay Capable of Simultaneous Typing of Multiple Pneumococcal Serotypes (Multibead Assay)", Clinical and Diagnostic Laboratory Immunology 7(3):486-489 (2000).

(Continued)

*Primary Examiner* — Galina M. Yakovleva
(74) *Attorney, Agent, or Firm* — Scully, Scott, Murphy & Presser, P.C.

(57) ABSTRACT

The present invention relates to methods of diagnosing lung cancer in a patient, as well as methods of monitoring the progression of lung cancer and/or methods of monitoring a treatment protocol of a therapeutic agent or a therapeutic regimen. The invention also relates to assay methods used in connection with the diagnostic methods described herein.

12 Claims, 1 Drawing Sheet

(56) References Cited

OTHER PUBLICATIONS

Saffar H. et al., "Expression of Galectin-3, nm-23, and Cyclooxygenase-2 Could Potentially Discriminate Between Benign and Malignant Pheochromocytoma", Am J Clin Pathol 135:454-460 (2011).
Skates S.J. et al., "Pooling of Case Specimens to Create Standard Serum Sets for Screening Cancer Biomarkers", Cancer Epidemiol Biomarkers Prev. 16(2):334-341 (2007).
Stengelin M.K. et al., "Multiplex Panels for Cancer-Associated Biomarkers: Quantify 40 Biomarkers from 40 uL of Serum or Plasma", (1 page) posted on Internet on Apr. 8, 2013.
Vignali D.A.A., "Multiplexed Particle-Based Flow Cytometric Assays", Journal of Immunological Methods 243:243-255 (2000).
Walt D.R., "Molecular Biology: Bead-Based Fiber-Optic Arrays", Science 287(5452):451-452 (2000).
The National Lung Screening Trial Research Team, "Reduced Lung-Cancer Mortality with Low-Dose Computed Tomographic Screening", The New England Journal of Medicine 365(5):395-409 (Aug. 4, 2011).
Product Insert, "MSD® 96-Well MULTI-ARRAY® and MULTI-SPOT® Human Cytokine Assays: Base Kit", (17 pages) created on Internet Feb. 8, 2011, modified Mar. 8, 2011.
"Quick Reference Sheet Identifying Abstract Ideas", retrieved on Nov. 19, 2019 (Jul. 2018).
U.S. Office Action dated Nov. 26, 2019 received in U.S. Appl. No. 15/813,418.
Final U.S. Office Action dated Aug. 21, 2017 received in U.S. Appl. No. 14/447,691.
U.S. Office Action dated Mar. 7, 2017 received in U.S. Appl. No. 14/447,691.
Final U.S. Office Action dated Mar. 30, 2016 received in U.S. Appl. No. 14/447,691.
Final U.S. Office Action dated Mar. 21, 2016 received in U.S. Appl. No. 14/447,691.
U.S. Office Action dated Nov. 2, 2015 received in U.S. Appl. No. 14/447,691.

* cited by examiner

Table 4.

LUNG CANCER BIOMARKERS

CROSS REFERENCE TO RELATED APPLICATIONS

The present application is a continuation of U.S. Ser. No. 15/813,418, filed Nov. 15, 2017, which is divisional application of U.S. Ser. No. 14/447,691, filed Jul. 31, 2014, now abandoned, which claims benefit of U.S. Provisional Application No. 61/945,006, filed Feb. 26, 2014; U.S. Provisional Application No. 61/860,958, filed Aug. 1, 2013; and the disclosures of which are incorporated herein by reference in their entireties.

STATEMENT REGARDING FEDERALLY-SPONSORED RESEARCH

This invention was made with government support under HHSN261201000018C awarded by the National Institutes of Health. The government has certain rights in the invention.

FIELD OF THE INVENTION

This application relates to assay methods useful in the detection and treatment of lung cancer.

BACKGROUND OF THE INVENTION

Challenges in the field of oncology include the lack of efficient means for early cancer detection and for specific cancer subtyping and for measuring and/or predicting responsiveness to therapy. There is a need for new cancer biomarkers that can provide early and specific diagnosis of cancer and enable targeted therapy and prognosis. The need for new diagnostics has been the impetus behind many initiatives targeting the discovery and development of new biomarkers for cancer. The hope is that the identification of suitable biomarkers will allow for the development of early cancer detection screening tests and will lead to improved cancer therapy and a reduction in the mortality associated with many cancers.

Currently, no efficient diagnostic tool for early detection of lung cancer is available, and in most cases lung cancer is asymptomatic during the early stages. As a result, a majority of patients present with stage III and IV disease, resulting in a 5-year survival rate that is <15%, in marked contrast to survival rates of 60-80% for cancer that had been detected in stage 1A.

SUMMARY OF THE INVENTION

The invention provides a method for evaluating the efficacy of a treatment regimen in a patient diagnosed with lung cancer, said method comprising
 (a) obtaining a test sample from a patient undergoing said treatment regimen for lung cancer,
 (b) measuring a level of a biomarker in said test sample, wherein said biomarker comprises MDC, NME-2, KGF, PIGF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, EPO, MMP-2, EGFR, MMP-3, ErbB2, cytokeratin-19, E-cadherin, IL-6, osteopontin, cKit, uPA, NSE, cMET, MDC, Flt-1, CEA, cytokeratin-8, KGF, S100A6, IL2-R, and combinations thereof;
 (c) comparing said level to a normal control level of said biomarker; and
 (d) evaluating from said comparing step (c) whether said patient is responsive to said treatment regimen.

An alternative method is provided that includes evaluating the efficacy of a treatment regimen in a patient diagnosed with lung cancer, said method comprising
 (a) ordering a test comprising a measurement of a level of a biomarker in a test sample obtained from a patient undergoing said treatment regimen for lung cancer, wherein said biomarker comprises MDC, NME-2, KGF, PIGF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, EPO, MMP-2, EGFR, MMP-3, ErbB2, cytokeratin-19, E-cadherin, IL-6, osteopontin, cKit, uPA, NSE, cMET, MDC, Flt-1, CEA, cytokeratin-8, KGF, S100A6, IL2-R, and combinations thereof;
 (b) comparing said level to a normal control level of said biomarker; and
 (c) evaluating from said comparing step (b) whether said patient is responsive to said treatment regimen.

Still further, the invention contemplates a method of administering a treatment regimen to a patient in need thereof for treating lung cancer, comprising:
 (a) obtaining a test sample from a patient undergoing said treatment regimen for lung cancer;
 (b) measuring a level of a biomarker in said test sample, wherein said biomarker comprises MDC, NME-2, KGF, PIGF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, EPO, MMP-2, EGFR, MMP-3, ErbB2, cytokeratin-19, E-cadherin, IL-6, osteopontin, cKit, uPA, NSE, cMET, MDC, Flt-1, CEA, cytokeratin-8, KGF, S100A6, IL2-R, and combinations thereof;
 (c) comparing said level to a normal control level of said biomarker;
 (d) evaluating from said comparing step (c) whether said patient is responsive to said treatment regimen; and
 (e) adjusting said treatment regimen based on said evaluating step (d).

Moreover, the invention includes a method of administering a treatment regimen to a patient in need thereof for treating lung cancer, comprising:
 (a) obtaining a test sample from a patient prior to the commencement of said treatment regimen for lung cancer;
 (b) measuring a level of a biomarker in said test sample, wherein said biomarker comprises MDC, NME-2, KGF, PIGF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, EPO, MMP-2, EGFR, MMP-3, ErbB2, cytokeratin-19, E-cadherin, IL-6, osteopontin, cKit, uPA, NSE, cMET, MDC, Flt-1, CEA, cytokeratin-8, KGF, S100A6, IL2-R, and combinations thereof;
 (c) comparing said level to a normal control level of said biomarker,
 (d) evaluating from said comparing step (c) whether said patient will be responsive to said treatment regimen; and
 (e) administering said treatment regimen based on said evaluating step (d).

Another embodiment of the invention is a method of administering a treatment regimen to a patient in need thereof for treating lung cancer, comprising:

(a) evaluating a level of a biomarker in a test sample obtained from a patient undergoing said treatment regimen for lung cancer relative to a normal control level of said biomarker, wherein said biomarker comprises MDC, NME-2, KGF, PIGF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, EPO, MMP-2, EGFR, MMP-3, ErbB2, cytokeratin-19, E-cadherin, IL-6, osteopontin, cKit, uPA, NSE, cMET, MDC, Flt-1, CEA, cytokeratin-8, KGF, S100A6, IL2-R, and combinations thereof; and (b) adjusting said treatment regimen based on said evaluating step (a).

An alternative embodiment of the invention is a method of administering a treatment regimen to a patient in need thereof for treating lung cancer, comprising:

(a) evaluating a level of a biomarker in a test sample obtained from a patient prior to the commencement of said treatment regimen for lung cancer relative to a normal control level of said biomarker, wherein said biomarker comprises MDC, NME-2, KGF, PIGF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, EPO, MMP-2, EGFR, MMP-3, ErbB2, cytokeratin-19, E-cadherin, IL-6, osteopontin, cKit, uPA, NSE, cMET, MDC, Flt-1, CEA, cytokeratin-8, KGF, S100A6, IL2-R, and combinations thereof; and (b) administering said treatment regimen based on said evaluating step (a).

A multiplexed assay kit is also contemplate that can be used to evaluate the efficacy of a treatment regimen in a patient diagnosed with lung cancer, said kit is configured to measure a level of a plurality of biomarkers in a patient sample, said plurality of biomarkers comprises MDC, NME-2, KGF, PIGF, Ft-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, EPO, MMP-2, EGFR, MMP-3, ErbB2, cytokeratin-19, E-cadherin, IL-6, osteopontin, cKit, uPA, NSE, cMET, MDC, Flt-1, CEA, cytokeratin-8, KGF, S100A6, IL2-R, and combinations thereof.

In a specific embodiment, a kit is provided for the analysis of a lung cancer panel comprising (a) a multi-well assay plate comprising a plurality of wells, each well comprising at least four discrete binding domains to which capture antibodies to the following human analytes are bound: MDC, NME-2, KGF, PIGF, Ft-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, EPO, MMP-2, EGFR, MMP-3, ErbB2, cytokeratin-19, E-cadherin, IL-6, osteopontin, cKit, uPA, NSE, cMET, MDC, Flt-1, CEA, cytokeratin-8, KGF, S100A6, IL2-R, and combinations thereof;

(b) in one or more vials, containers, or compartments, a set of labeled detection antibodies specific for said human analytes; and (c) in one or more vials, containers, or compartments, a set of calibrator proteins.

In one embodiment, the methods and kits of the invention are configured to measure one or more of the following biomarkers: Flt-3L, MMP-2, EGFR, MMP-3, ErbB2, NME-2, cytokeratin 19, E-cadherin, IL-6, osteopontin, cKit, uPA, NSE, VEGF-D, cMET, and MDC.

In an alternative or additional embodiment, the methods and kits of the invention are configured to measure one or more of the following biomarkers: Flt-3L, EGFR, MMP-3, ErbB2, cytokeratin 19, IL-6, osteopontin, cKit, Fit-1, KGF, cytokeratin-8, HGF, GPI, S100A6, and IL2-R.

In a particular embodiment, the methods and kits of the invention are configured to measure the following serum biomarkers: Flt-3L, EGFR, MMP-3, and NME-2. In an alternative or additional embodiment, the methods and kits of the invention are configured to measure the following plasma biomarkers: Flt-3L, cytokeratin-19, Flt-1, KGF, and HGF.

The invention also provides a multiplexed assay kit and methods of using that kit to evaluate biomarker levels in a patient sample, said kit is configured to measure a level of a plurality of biomarkers in a patient serum sample, said plurality of biomarkers comprises Flt-3L, EGFR, MMP-3, and NME-2, and combinations thereof.

Another embodiment is a methods and kits for the analysis of a lung cancer panel, wherein the kit comprises (a) a multi-well assay plate comprising a plurality of wells, each well comprising at least four discrete binding domains to which capture antibodies to the following human serum analytes are bound: Flt-3L, EGFR, MMP-3, and NME-2, and combinations thereof;

(b) in one or more vials, containers, or compartments, a set of labeled detection antibodies specific for said human analytes; and (c) in one or more vials, containers, or compartments, a set of calibrator proteins.

Moreover, the invention includes a multiplexed assay kit methods of using that kit to evaluate biomarker levels in a patient sample, said kit is configured to measure a level of a plurality of biomarkers in a patient plasma sample, said plurality of biomarkers comprises Flt-3L, cytokeratin-19, Flt-1, KGF, and HGF, and combinations thereof.

Still further, the invention includes methods and kits for the analysis of a lung cancer panel comprising (a) a multi-well assay plate comprising a plurality of wells, each well comprising at least four discrete binding domains to which capture antibodies to the following human plasma analytes are bound: Flt-3L, cytokeratin-19, Flt-1, KGF, and HGF, and combinations thereof;

(b) in one or more vials, containers, or compartments, a set of labeled detection antibodies specific for said human analytes; and (c) in one or more vials, containers, or compartments, a set of calibrator proteins.

BRIEF DESCRIPTION OF THE FIGURES

FIG. 1 shows the results of a correlation analysis of selected biomarkers tested.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

As used herein, the term "sample" is intended to mean any biological fluid, cell, tissue, organ or combinations or portions thereof, which includes or potentially includes a biomarker of a disease of interest. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. In one embodiment, the samples that are analyzed in the assays of the present invention are blood, peripheral blood mononuclear cells (PBMC), isolated blood cells, serum and plasma. Other suitable samples include biopsy tissue, intestinal mucosa, saliva, cerebral spinal fluid, and urine. In a preferred embodiment, samples used in the assays of the invention are serum samples.

A "biomarker" is a substance that is associated with a particular disease. A change in the levels of a biomarker may correlate with the risk or progression of a disease or with the susceptibility of the disease to a given treatment. A biomarker may be useful in the diagnosis of disease risk or the presence of disease in an individual, or to tailor treatments for the disease in an individual (choices of drug treatment or administration regimes and/or to predict responsiveness or non-responsiveness to a particular therapeutic regimen). In evaluating potential drug therapies, a biomarker may be used as a surrogate for a natural endpoint such as survival or irreversible morbidity. If a treatment alters a biomarker that has a direct connection to improved health, the biomarker serves as a "surrogate endpoint" for evaluating clinical benefit. A sample that is assayed in the diagnostic methods of the present invention may be obtained from any suitable patient, including but not limited to a patient suspected of having lung cancer or a patient having a predisposition to lung cancer. The patient may or may not exhibit symptoms associated with one or more of these conditions.

"Level" refers to the amount, concentration, or activity of a biomarker. The term "level" may also refer to the rate of change of the amount, concentration or activity of a biomarker. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a biomarker accumulated in a cell, including, for example, the amount of particular post-synthetic modifications of a biomarker such as a polypeptide, nucleic acid or small molecule. The term can be used to refer to an absolute amount of a biomarker in a sample or to a relative amount of the biomarker, including amount or concentration determined under steady-state or non-steady-state conditions. Level may also refer to an assay signal that correlates with the amount, concentration, activity or rate of change of a biomarker. The level of a biomarker can be determined relative to a control marker or an additional biomarker in a sample.

It will be understood to one of ordinary skill in the art that lung cancer is divided into two major subtypes, non-small cell lung cancer (NSCLC) and small cell lung cancer (SCLC). Each type of lung cancer grows and spreads in different ways and may be treated differently. There are three subtypes of NSCLC: squamous cell carcinoma, adenocarcinoma, and large cell undifferentiated carcinoma. The subtype of NSCLC does not influence treatment options. SCLC is often referred to as oat cell cancer, small cell undifferentiated carcinoma, and poorly differentiated neuroendocrine carcinoma. As described in more detail below, a set of novel biomarkers of lung cancer has been identified, MDC, NME-2, KGF, PlGF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, EPO, MMP-2, EGFR, MMP-3, ErbB2, cytokeratin-19, E-cadherin, IL-6, osteopontin, cKit, uPA, NSE, cMET, MDC, Flt-1, CEA, cytokeratin-8, KGF, S100A6, IL2-R, and combinations thereof, and these biomarkers can be used, alone or in combination with one or more additional lung cancer biomarkers, e.g., adiponectin, IL-10, VEGF, ENA-78, PPP2R4, RANTES, SAT-1, ALK, KRAS, p53, CYFRA21-1, LKKB1, or Neuron-specific enolase, for the diagnosis of lung cancer and/or to assess susceptibility of lung cancer in a patient to a treatment regimen. In a preferred embodiment, the set of biomarkers include Flt-3L, MMP-2, EGFR, MMP-3, ErbB2, NME-2, cytokeratin 19, E-cadherin, IL-6, osteopontin, cKit, uPA, NSE, VEGF-D, cMET, MDC, cytokeratin-8, HGF, GPI, S100A6, IL2-R, and combinations thereof, and these biomarkers or the broader set identified above, can be used alone or in combination with one or more of the following: NSE, CEA, Cyfra 21.1, Ca19.9, Her-2, AFP, or Ca125. In one embodiment, the following biomarkers are analyzed in serum samples; Ft-3L, MMP-2, EGFR, MMP-3, ErbB2, NME-2, cytokeratin 19, E-cadherin, IL-6, osteopontin, cKit, uPA, NSE, VEGF-D, cMET, MDC, and combinations thereof. Additionally or alternatively, the following biomarkers are analyzed in plasma samples: Flt-3L, EGFR, MMP-3, ErbB2, cytokeratin 19, IL-6, osteopontin, cKit, Flt-1, KGF, cytokeratin-8, HGF, GPI, S100A6, IL2-R, and combinations thereof.

These biomarkers can be used in a diagnostic method, alone or in combination with other biomarkers for lung cancer and/or diagnostic tests for lung cancer, to diagnose lung cancer in a patient, and in one embodiment, to differentially diagnose the different forms of lung cancer in a patient, i.e., non-small cell lung cancer (NSCLC) vs. small cell lung cancer (SCLC). Alternatively or additionally, these biomarkers can be used to monitor a therapeutic regimen used for the treatment of lung cancer to assess the efficacy of the regimen for a given patient.

The method of the present invention can include assessing the efficacy of a therapeutic regimen for lung cancer and/or the susceptibility of a patient to a therapeutic regimen. NSCLC and SCLC are often treated by combining one or more chemotherapeutic agents and chemotherapy is often administered in cycles, with each period of treatment followed by a recovery period. Chemotherapy cycles generally last about 21 to 28 days, and initial treatment typically involves 4-6 cycles. The drug combinations most frequently used for first line chemotherapy for NSCLC are cisplatin or carboplatin combined with one or more of the following agents: bevacizumab, gefitinib, erlotinib hydrochloride, paclitaxel, docetaxel, gemcitabine, vinorelbine, irinotecan, etoposide, or vinblastine. The drug combinations most frequently used for initial chemotherapy for SCLC are cisplatin and etoposide or carboplatin and etoposide (for limited stage), and cisplatin and etoposide, carboplatin and etoposide, or cisplatin or irinotecan (for extensive stage). A comprehensive overview of the diagnosis and treatment of NSCLC and SCLC can be found at www.cancer.gov.

The therapeutic regimen may include administration of a therapeutic agent or a combination of therapeutic agents to a patient one or more times over a given time period. This treatment regimen may be accompanied by the administration of one or more additional therapeutic or palliative agents. The level(s) of biomarkers may be measured before treatment, one or more times during the administration period, and/or after treatment is suspended. Therefore, the method may include measuring an interim level of a biomarker during the therapeutic regimen and the method includes evaluating biomarker levels by comparing that level, the interim level and the baseline level. In addition, the level of a biomarker may be determined at any time point before and/or after initiation of treatment. In one embodiment, the biomarker is used to gauge the efficacy of a therapeutic regimen. Therefore, the method of the present invention may include measuring a baseline level(s) of a biomarker before a therapeutic regimen is initiated, and the method includes evaluating biomarker levels by comparing the level and the baseline level.

Still further, the method can include measuring a level(s) of a biomarker before a therapeutic regimen is initiated to predict whether a lung cancer will be responsive or nonresponsive to a given therapeutic regimen. The method may further comprise modifying the therapeutic regimen based on the level(s) of a biomarker observed during this preliminary and/or interim measuring step, e.g., increasing or decreasing the dosage, frequency, or route of administration of a therapeutic agent, adding an additional therapeutic agent and/or palliative agent to a treatment regimen, or if the therapeutic regimen includes the administration of two or more therapeutic and/or palliative agents, the treatment regimen may be modified to eliminate one or more of the therapeutic and/or palliative agents used in the combination therapy.

Still further, the method can include comparing the level of a biomarker to a detection cut-off level, wherein a level above the detection cut-off level is indicative of lung cancer. Alternatively, the evaluating step comprises comparing a level of a biomarker to a detection cut-off level, wherein a level below the detection cut-off level is indicative of lung cancer. In one embodiment of the present invention, the level of a biomarker is compared to a detection cut-off level or range, wherein the biomarker level above or below the detection cut-off level (or within the detection cut-off range) is indicative of lung cancer. Furthermore, the levels of two or more biomarkers may both be used to make a determination. For example, i) having a level of at least one of the markers above or below a detection cut-off level (or within a detection cut-off range) for that marker is indicative of lung cancer ii) having the level of two or more (or all) of the markers above or below a detection cut-off level (or within a detection cut-off range) for each of the markers is indicative of lung cancer; or iii) an algorithm based on the levels of the multiple markers is used to determine if lung cancer is present.

The methods of the invention can be used alone or in combination with other diagnostic tests or methods to diagnose a patient with lung cancer. The following tests are generally used by clinicians to diagnose a patient with lung cancer, and this set of tests can be considered in combination with a diagnostic method including a screen for the biomarkers identified here to diagnose a patient with lung cancer.

Chest x-ray
CT or CAT scan
low-dose helical CT scan
MRI
PET scan
Bone scan
Sputum cytology
Bronchoscopy
Needle biopsy
Thoracentesis In one embodiment, one or more of the biomarkers identified herein can be used in combination with other diagnostic techniques to aide in treatment decisions, e.g., in combination with a CT scan and/or patient history (including but not limited to, whether the patient has a history of lung cancer or related cancer, whether the patient has a family history of lung cancer or related cancer and the relationship of that relative(s) to the patient, whether the patient is a smoker, currently or in the past (and how far in the past), and if so, how frequently the patient smoker per day), or whether the patient is exposed to second hand smoke and with what frequency. For example, an assay of a patient sample for one or more of the biomarkers identified herein can be used to decide whether a patient with a history of smoking or exposure to an individual that smokes should receive a CT scan. Alternatively or additionally, an assay of a patient sample for one or more of the biomarkers identified herein can be used to decide whether a patient with a questionable CT scan should receive more or less aggressive follow-up tests. Reference is made to N. Engl. J. Med. 2011; 365: 395-409, the disclosure of which is incorporated by reference in its entirety.

As described herein, the measured levels of one or more biomarkers may be used to detect or monitor lung cancer and/or to determine the responsiveness of lung cancer to a specific treatment regimen. The specific methods/algorithms for using biomarker levels to make these determinations, as described herein, may optionally be implemented by software running on a computer that accepts the biomarker levels as input and returns a report with the determinations to the user. This software may run on a standalone computer or it may be integrated into the software/computing system of the analytical device used to measure the biomarker levels or, alternatively, into a laboratory information management system (LIMS) into which crude or processed analytical data is entered. In one embodiment, biomarkers are measured in a point-of-care clinical device which carries out the appropriate methods/algorithms for detecting, monitoring or determining the responsiveness of a disease and which reports such determination(s) back to the user.

According to one aspect of the invention, the level(s) of biomarker(s) are measured in samples collected from individuals clinically diagnosed with, suspected of having or at risk of developing lung cancer. Initial diagnosis may have been carried out using conventional methods. The level(s) of biomarker(s) are also measured in healthy individuals. Specific biomarkers valuable in distinguishing between normal and diseased patients are identified by visual inspection of the data, for example, by visual classification of data plotted on a one-dimensional or multidimensional graph, or by using statistical methods such as characterizing the statistically weighted difference between control individuals and diseased patients and/or by using Receiver Operating Characteristic (ROC) curve analysis. A variety of suitable methods for identifying useful biomarkers and setting detection thresholds/algorithms are known in the art and will be apparent to the skilled artisan.

For example and without limitation, diagnostically valuable biomarkers may be first identified using a statistically weighted difference between control individuals and diseased patients, calculated as $$\frac{D-N}{\sqrt{\sigma_D * \sigma_N}}$$

wherein D is the median level of a biomarker in patients diagnosed as having, for example, lung cancer, N is the median (or average) of the control individuals, $\sigma_D$ is the standard deviation of D and $\sigma_N$ is the standard deviation of N. The larger the magnitude, the greater the statistical difference between the diseased and normal populations.

According to one embodiment of the invention, biomarkers resulting in a statistically weighted difference between control individuals and diseased patients of greater than, e.g., 1, 1.5, 2, 2.5 or 3 could be identified as diagnostically valuable markers.

Another method of statistical analysis for identifying biomarkers is the use of z-scores, e.g., as described in Skates et al. (2007) Cancer Epidemiol. Biomarkers Prev. 16(2):334-341.

Another method of statistical analysis that can be useful in the inventive methods of the invention for determining the efficacy of particular candidate analytes, such as particular biomarkers, for acting as diagnostic marker(s) is ROC curve analysis. An ROC curve is a graphical approach to looking at the effect of a cut-off criterion, e.g., a cut-off value for a diagnostic indicator such as an assay signal or the level of an analyte in a sample, on the ability of a diagnostic to correctly identify positive or negative samples or subjects. One axis of the ROC curve is the true positive rate (TPR, i.e., the probability that a true positive sample/subject will be correctly identified as positive, or alternatively, the false negative rate (FNR=1−TPR, the probability that a true positive sample/subject will be incorrectly identified as a negative). The other axis is the true negative rate, i.e., TNR, the probability that a true negative sample will be correctly identified as a negative, or alternatively, the false positive rate (FPR=1−TNR, the probability that a true negative sample will be incorrectly identified as positive). The ROC curve is generated using assay results for a population of samples/subjects by varying the diagnostic cut-off value used to identify samples/subjects as positive or negative and plotting calculated values of TPR or FNR and TNR or FPR for each cut-off value. The area under the ROC curve (referred to herein as the AUC) is one indication of the ability of the diagnostic to separate positive and negative samples/subjects. In one embodiment, a biomarker provides an AUC≥0.7. In another embodiment, a biomarker provides an AUC≥20.8. In another embodiment, a biomarker provides an AUC≥0.9.

Diagnostic indicators analyzed by ROC curve analysis may be a level of an analyte, e.g., a biomarker, or an assay signal. Alternatively, the diagnostic indicator may be a function of multiple measured values, for example, a function of the level/assay signal of a plurality of analytes, e.g., a plurality of biomarkers, or a function that combines the level or assay signal of one or more analytes with a patient's scoring value that is determined based on visual, radiological and/or histological evaluation of a patient. The multi-parameter analysis may provide more accurate diagnosis relative to analysis of a single marker.

Candidates for a multi-analyte panel could be selected by using criteria such as individual analyte ROC areas, median difference between groups normalized by geometric interquartile range (IQR) etc. The objective is to partition the analyte space to improve separation between groups (for example, normal and disease populations) or to minimize the misclassification rate.

One approach is to define a panel response as a weighted combination of individual analytes and then compute an objective function like ROC area, product of sensitivity and specificity, etc. See e.g., WO 2004/058055, as well as US2006/0205012, the disclosures of which are incorporated herein by reference in their entireties.

The assays of the present invention may be conducted by any suitable method. In one embodiment, biomarker levels are measured in a single sample, and those measurement may be conducted in a single assay chamber or assay device, including but not limited to a single well of an assay plate, a single assay cartridge, a single lateral flow device, a single assay tube, etc. Biomarker levels may be measured using any of a number of techniques available to the person of ordinary skill in the art, e.g., direct physical measurements (e.g., mass spectrometry) or binding assays (e.g., immunoassays, agglutination assays and immunochromatographic assays). The method may also comprise measuring a signal that results from a chemical reactions, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

Binding assays for measuring biomarker levels may use solid phase or homogenous formats. Suitable assay methods include sandwich or competitive binding assays. Examples of sandwich immunoassays are described in U.S. Pat. Nos. 4,168,146 and 4,366,241, both of which are incorporated herein by reference in their entireties. Examples of competitive immunoassays include those disclosed in U.S. Pat. Nos. 4,235,601, 4,442,204 and 5,208,535, each of which are incorporated herein by reference in their entireties.

Multiple biomarkers may be measured using a multiplexed assay format, e.g., multiplexing through the use of binding reagent arrays, multiplexing using spectral discrimination of labels, multiplexing of flow cytometric analysis of binding assays carried out on particles, e.g., using the Luminex® system. Suitable multiplexing methods include array based binding assays using patterned arrays of immobilized antibodies directed against the biomarkers of interest. Various approaches for conducting multiplexed assays have been described (See e.g., US 20040022677; US 20050052646; US 20030207290; US 20030113713; US 20050142033; and US 20040189311, each of which is incorporated herein by reference in their entireties. One approach to multiplexing binding assays involves the use of patterned arrays of binding reagents, e.g., U.S. Pat. Nos. 5,807,522 and 6,110,426; Delehanty J-B., Printing functional protein microarrays using piezoelectric capillaries, Methods Mol. Bio. (2004) 278: 135-44; Lue R Y et al., Site-specific immobilization of biotinylated proteins for protein microarray analysis, Methods Mol. Biol. (2004) 278:

85-100; Lovett, Toxicogenomics: Toxicologists Brace for Genomics Revolution, Science (2000) 289: 536-537; Berns A, Cancer: Gene expression in diagnosis, nature (2000), 403, 491-92; Walt, Molecular Biology: Bead-based Fiber-Optic Arrays, Science (2000) 287: 451-52 for more details). Another approach involves the use of binding reagents coated on beads that can be individually identified and interrogated. See e.g., WO 9926067, which describes the use of magnetic particles that vary in size to assay multiple analytes; particles belonging to different distinct size ranges are used to assay different analytes. The particles are designed to be distinguished and individually interrogated by flow cytometry. Vignali has described a multiplex binding assay in which 64 different bead sets of microparticles are employed, each having a uniform and distinct proportion of two dyes (Vignali, D. A A, "Multiplexed Particle-Based Flow Cytometric Assays" J. ImmunoL Meth. (2000) 243: 243-55). A similar approach involving a set of 15 different beads of differing size and fluorescence has been disclosed as useful for simultaneous typing of multiple pneumococcal serotypes (Park, M. K et al., "A Latex Bead-Based Flow Cytometric Immunoassay Capable of Simultaneous Typing of Multiple Pneumococcal Serotypes (Multibead Assay)" Clin. Diag. Lab ImmunoL (2000) 7: 4869). Bishop, J E et al. have described a multiplex sandwich assay for simultaneous quantification of six human cytokines (Bishop, L E. et al., "Simultaneous Quantification of Six Human Cytokines in a Single Sample Using Microparticle-based Flow Cytometric Technology," Clin. Chem (1999) 45:1693-1694).

A diagnostic test may be conducted in a single assay chamber, such as a single well of an assay plate or an assay chamber that is an assay chamber of a cartridge. The assay modules, e.g., assay plates or cartridges or multi-well assay plates), methods and apparatuses for conducting assay measurements suitable for the present invention are described for example, in US 20040022677; US 20050052646; US 20050142033; US 20040189311, each of which is incorporated herein by reference in their entireties. Assay plates and plate readers are commercially available (MULTI-SPOT® and MULTI-ARRAY® plates and SECTOR® instruments, Meso Scale Discovery, a division of Meso Scale Diagnostics, LLC, Rockville, Md.).

The present invention relates to a kit for the analysis of a panel of target analytes. The kit is preferably configured to conduct a multiplexed assay of two or more analytes. The kit can include (a) a single panel arrayed on a multi-well plate which is configured to be used in an electrochemiluminescence assay, as well as (b) associated consumables, e.g., detection antibodies, calibrators, and optional diluents and/or buffers. Alternatively, the multi-well plates and associated consumables can be provided separately.

The panel is preferably configured in a multi-well assay plate including a plurality of wells, each well having an array with "spots" or discrete binding domains. Preferably, the array includes one, four, seven, ten, sixteen, or twenty-five binding domains, and most preferably, the array includes one, four, seven, or ten binding domains. A capture antibody to each analyte is immobilized on a binding domain in the well and that capture antibody is used to detect the presence of the target analyte in an immunoassay. Briefly, a sample suspected of containing that analyte is added to the well and if present, the analyte binds to the capture antibody at the designated binding domain. The presence of bound analyte on the binding domain is detected by adding labeled detection antibody. The detection antibody also binds to the analyte forming a "sandwich" complex (capture antibody—analyte—detection antibody) on the binding domain.

The multiplexed immunoassay kits described herein allow a user to simultaneously quantify multiple biomarkers. The panels are selected and optimized such that the individual assays function well together. The sample may require dilution prior to being assayed. Sample dilutions for specific sample matrices of interest are optimized for a given panel to minimize sample matrix effects and to maximize the likelihood that all the analytes in the panel will be within the dynamic range of the assay. In a preferred embodiment, all of the analytes in the panel are analyzed with the same sample dilution in at least one sample type. In another preferred embodiment, all of the analytes in a panel are measured using the same dilution for most sample types.

For a given panel, the detection antibody concentration and the number of labels per protein (LP ratio) for the detection antibody are adjusted to bring the expected levels of all analytes into a quantifiable range at the same sample dilution. If one wants to increase the high end of the quantifiable range for a given analyte, then the L/P can be decreased and/or the detection antibody concentration is decreased. On the other hand, if one wants to increase the lower end of the quantifiable range, the L/P can be increased, the detection antibody concentration can be increased if it is not at the saturation level, and/or the background signal can be lowered.

Calibration standards for use with the assay panels are selected to provide the appropriate quantifiable range with the recommended sample dilution for the panel. The calibration standards have known concentrations of one of more of the analytes in the panel. Concentrations of the analytes in unknown samples are determined by comparison to these standards. In one embodiment, calibration standards comprise mixtures of the different analytes measured by an assay panel. Preferably, the analyte levels in a combined calibrator are selected such that the assay signals for each analyte are comparable, e.g., within a factor of two, a factor of five or a factor of 10. In another embodiment, calibration standards include mixtures of analytes from multiple different assay panels.

A calibration curve may be fit to the assay signals measured with calibration standards using, e.g., curve fits known in the art such as linear fits, 4-parameter logistic (4-PL) and 5-parameter (5-PL) fits. Using such fits, the concentration of analytes in an unknown sample may be determined by backfitting the measured assay signals to the calculated fits. Measurements with calibration standards may also be used to determine assay characteristics such as the limit of detection (LOD), limit of quantification (LOQ), dynamic range, and limit of linearity (LOL).

A kit can include the following assay components: a multi-well assay plate configured to conduct an immunoassay for one of the panels described herein, a set of detection antibodies for the analytes in the panel (wherein the set comprises individual detection antibodies and/or a composition comprising a blend of one or more individual detection antibodies), and a set of calibrators for the analytes in the panel (wherein the set comprises individual calibrator protein compositions and/or a composition comprising a blend of one or more individual calibrator proteins). The kit can also include one of more of the following additional components: a blocking buffer (used to block assay plates prior to addition of sample), an antibody diluent (used to dilute stock detection antibody concentrations to the working concentration), an assay diluent (used to dilute samples), a calibrator diluent (used to dilute or reconstitute calibration standards) and a read buffer (used to provide the appropriate environment for detection of assay labels, e.g., by an ECL measurement). The antibody and assay diluents are selected to reduce background, optimize specific signal, and reduce assay interference and matrix effect. The calibrator diluent is optimized to yield the longest shelf life and retention of calibrator activity. The blocking buffer should be optimized to reduce background. The read buffer is selected to yield the appropriate sensitivity, quantifiable range, and slowest off-rate.

The reagent components of the kit can be provided as liquid reagents, lyophilized, or combinations thereof, diluted or undiluted, and the kit includes instructions for appropriate preparation of reagents prior to use. In a preferred embodiment, a set of detection antibodies are included in the kit comprising a plurality of individual detection antibody compositions in liquid form. Moreover, the set of calibrators provided in the kit preferably comprise a lyophilized blend of calibrator proteins. Still further, the kit includes a multi-well assay plate that has been pre-coated with capture antibodies and exposed to a stabilizing treatment to ensure the integrity and stability of the immobilized antibodies.

As part of a multiplexed panel development, assays are optimized to reduce calibrator and detection antibody non-specific binding. In sandwich immunoassays, specificity mainly comes from capture antibody binding. Some considerations for evaluating multiplexed panels include: (a) detection antibody non-specific binding to capture antibodies is reduced to lower background of assays in the panel, and this can be achieved by adjusting the concentrations and L/P of the detection antibodies; (b) non-specific binding of detection antibodies to other calibrators in the panel is also undesirable and should be minimized; (c) non-specific binding of other calibrators in the panel and other related analytes should be minimized; if there is calibrator non-specific binding, it can reduce the overall specificity of the assays in the panel and it can also yield unreliable results as there will be calibrator competition to bind the capture antibody.

Different assays in the panel may require different incubation times and sample handling requirements for optimal performance. Therefore, the goal is to select a protocol that's optimized for most assays in the panel. Optimization of the assay protocol includes, but is not limited to, adjusting one or more of the following protocol parameters: timing (incubation time of each step), preparation procedure (calibrators, samples, controls, etc.), and number of wash steps.

The reagents used in the kits, e.g., the detection and capture antibodies and calibrator proteins, are preferably subjected to analytical testing and meet or exceed the specifications for those tests. The analytical tests that can be used to characterize kit materials include but are not limited to, CIEF, DLS, reducing and/or non-reducing EXPERION™, denaturing SDS-PAGE, non-denaturing SDS-PAGE, SEC-MALS, and combinations thereof. In a preferred embodiment, the materials are characterized by CIEF, DLS, and reducing and non-reducing EXPERION™. One or more additional tests, including but not limited to denaturing SDS-PAGE, non-denaturing SDS-PAGE, SEC-MALS, and combinations thereof, can also be used to characterize the materials. In a preferred embodiment, the materials are also subjected to functional testing, i.e., a binding assay for the target analyte, as well as one or more characterization tests, such as those listed above. If the materials do not meet or exceed the specifications for the functional and/or characterization tests, they can be subjected to additional purification steps and re-tested. Each of these tests and the metrics applied to the analysis of raw materials subjected to these tests are described below:

Capillary Isoelectric Focusing (CIEF) is a technique commonly used to separate peptides and proteins, and it is useful in the detection of aggregates. During a CIEF separation, a capillary is filled with the sample in solution and when voltage is applied, the ions migrate to a region where they become neutral (pH=pI). The anodic end of the capillary sits in acidic solution (low pH), while the cathodic end sits in basic solution (high pH). Compounds of equal isoelectric points (pI) are "focused" into sharp segments and remain in their specific zone, which allows for their distinct detection based on molecular charge and isoelectric point. Each specific antibody solution will have a fingerprint CIEF that can change over time. When a protein solution deteriorates, the nature of the protein and the charge distribution can change. Therefore, CIEF is a particularly useful tool to assess the relative purity of a protein solution and it is a preferred method of characterizing the antibodies and calibrators in the plates and kits described herein. The metrics used in CIEF include pI of the main peak, the pI range of the solution, and the profile shape, and each of these measurements are compared to that of a reference standard.

Dynamic Light Scattering (DLS) is used to probe the diffusion of particulate materials either in solution or in suspension. By determining the rate of diffusion (the diffusion coefficient), information regarding the size of particles, the conformation of macromolecular chains, various interactions among the constituents in the solution or suspension, and even the kinetics of the scatterers can be obtained without the need for calibration. In a DLS experiment, the fluctuations (temporal variation, typically in a µs to ms time scale) of the scattered light from scatterers in a medium are recorded and analyzed in correlation delay time domain. Like CIEF, each protein solution will generate a fingerprint DLS for the particle size and it's ideally suited to detect aggregation. All IgGs, regardless of binding specificity, will exhibit the same DLS particle size. The metrics used to analyze a protein solution using DLS include percentage polydispersity, percentage intensity, percentage mass, and the radius of the protein peak. In a preferred embodiment, an antibody solution meets or exceeds one or more of the following DLS specifications: (a) radius of the antibody peak: 4-8 nm (antibody molecule size); (b) polydispersity of the antibody peak: <40% (measure of size heterogeneity of antibody molecules); (c) intensity of the antibody peak: >50% (if other peaks are present, then the antibody peak is the predominant peak); and (d) mass in the antibody peak: >50%.

Reducing and non-reducing gel electrophoresis are techniques well known in the art. The EXPERION™ (Bio-Rad Laboratories, Inc., www.bio-rad.com) automated electrophoresis station performs all of the steps of gel-based electrophoresis in one unit by automating and combining electrophoresis, staining, destaining, band detection, and imaging into a single step. It can be used to measure purity. Preferably, an antibody preparation is greater 50% pure by EXPERION™, more preferably, greater than 75% pure, and most preferably greater than 80% pure. Metrics that are applied to protein analysis using non-reducing EXPERION™ include percentage total mass of protein, and for reducing EXPERION™ they include percentage total mass of the heavy and light chains in an antibody solution, and the heavy to light chain ratio.

Multi-Angle Light Scattering (MALS) detection can be used in the stand-alone (batch) mode to measure specific or non-specific protein interactions, as well as in conjunction with a separation system such as flow field flow fractionation (FFF) or size exclusion chromatography (SEC). The combined SEC-MALS method has many applications, such as the confirmation of the oligomeric state of a protein, quantification of protein aggregation, and determination of protein conjugate stoichiometry. Preferably, this method is used to detect molecular weight of the components of a sample.

As used herein, a lot of kits comprise a group of kits comprising kit components that meet a set of kit release specifications. A lot can include at least 10, at least 100, at least 500, at least 1,000, at least 5,000, or at least 10,000 kits and a subset of kits from that lot are subjected to analytical testing to ensure that the lot meets or exceeds the release specifications. In one embodiment, the release specifications include but are not limited to kit processing, reagent stability, and kit component storage condition specifications. Kit processing specifications include the maximum total sample incubation time and the maximum total time to complete an assay using the kit. Reagent stability specifications include the minimum stability of each reagent component of the kit at a specified storage temperature. Kit storage condition specifications include the range of storage temperatures for all components of the kit, the maximum storage temperature for frozen components of the kit, and the maximum storage temperature for non-frozen components of the kit. A subset of kits in a lot is reviewed in relation to these specifications and the size of the subset depends on the lot size. In a preferred embodiment, for a lot of up to 300 kits, a sampling of 4-7 kits are tested; for a lot of 300-950 kits, a sampling of 8-10 kits are tested; and for a lot of greater than 950 kits, a sampling of 10-12 kits are tested. Alternatively or additionally, a sampling of up to 1-5% preferably up to 1-3%, and most preferably up to 2% is tested.

In addition, each lot of multi-well assay plates is preferably subjected to uniformity and functional testing. A subset of plates in a lot is subjected to these testing methods and the size of the subset depends on the lot size. In a preferred embodiment, for a lot of up to 300 plates, a sampling of 4-7 plates are tested; for a lot of 300-950 plates, a sampling of 8-10 plates are tested; and for a lot of greater than 950 plates, a sampling of 10-12 plates are tested. Alternatively or additionally, a sampling of up to 1-5% preferably up to 1-3%, and most preferably up to 2% is tested. The uniformity and functional testing specifications are expressed in terms of % CV, Coefficient of Variability, which is a dimensionless number defined as the standard deviation of a set of measurements, in this case, the relative signal detected from binding domains across a plate, divided by the mean of the set.

One type of uniformity testing is protein A/G testing. Protein A/G binding is used to confirm that all binding domains within a plate are coupled to capture antibody. Protein A/G is a recombinant fusion protein that combines IgG binding domains of Protein A and protein G and it binds to all subclasses of human IgG, as well as IgA, IgE, IgM and, to a lesser extent, IgD. Protein A/G also binds to all subclasses of mouse IgG but not mouse IgA, IgM, or serum albumin, making it particularly well suited to detect mouse monoclonal IgG antibodies without interference from IgA, IgM, and serum albumin that might be present in the sample matrix. Protein A/G can be labeled with a detectable moiety, e.g., a fluorescent, chemiluminescent, or electrochemiluminescent label, preferably an ECL label, to facilitate detection. Therefore, if capture antibody is adhered to a binding domain of a well, it will bind to labeled protein A/G, and the relative amount of capture antibody bound to the surface across a plate can be measured.

In addition to the uniformity testing described above, a uniformity metric for a subset of plates within a lot can be calculated to assess within-plate trending. A uniformity metric is calculated using a matrix of normalized signals from protein A/G and/or other uniformity or functional tests. The raw signal data is smoothed by techniques known in the art, thereby subtracting noise from the raw data, and the uniformity metric is calculated by subtracting the minimum signal in the adjusted data set from the maximum signal.

In a preferred embodiment, a subset of plates in a lot is subjected to protein A/G and functional testing and that subset meet or exceed the following specifications:

TABLE 1

Plate Metrics

| Metric | Preferred Specification for a subset of 96 well multi-well plates |
| --- | --- |
| Average intraplate CV | ≤10% |
| Maximum intraplate CV | ≤13% |
| Average Uniformity | ≤25% |
| Maximum Uniformity | ≤37% |
| CV of intraplate averages | ≤18% |
| Signal, lower boundary | >1500 |
| Signal, upper boundary | $<10^{(6)}$ |

As disclosed in U.S. Pat. No. 7,842,246 to Wohlstadter et al., the disclosure of which is incorporated herein by reference in its entirety, each plate consists of several elements, e.g., a plate top, a plate bottom, wells, working electrodes, counter electrodes, reference electrodes, dielectric materials, electrical connects, and assay reagents. The wells of the plate are defined by holes/openings in the plate top. The plate bottom can be affixed, manually or by automated means, to the plate top, and the plate bottom can serve as the bottom of the well. Plates may have any number of wells of any size or shape, arranged in any pattern or configuration, and they can be composed of a variety of different materials. Preferred embodiments of the invention use industry standard formats for the number, size, shape, and configuration of the plate and wells. Examples of standard formats include 96, 384, 1536, and 9600 well plates, with the wells configured in two-dimensional arrays. Other formats may include single well plates (preferably having a plurality of assay domains that form spot patterns within each well), 2 well plates, 6 well plates, 24 well plates, and 6144 well plates. Each well of the plate includes a spot pattern of varying density, ranging from one spot within a well to 2, 4, 7, 9, 10, 16, 25, etc., as described hereinabove.

Each plate is assembled according to a set of preferred specifications. In a preferred embodiment, a plate bottom meets or exceeds the following specifications:

TABLE 2

Plate bottom specifications

| Parameter | 96-well (round well) specifications in inches |
| --- | --- |
| Length range (C to C)* | 3.8904-3.9004 (A1-A12 and H1-H12) |
| Width range (C to C) | 2.4736-2.4836 (A1-A12 and H1-H12) |
| Well to well spacing | 0.3513-0.3573 |

*C to C well distance is the center of spot to center of spot distance between the outermost wells of a plate.

In a further preferred embodiment, the plate also meets or exceeds defined specifications for alignment of a spot pattern within a well of the plate. These specifications include three parameters: (a) Δx, the difference between the center of the spot pattern and the center of the well along the x axis of the plate (column-wise, long axis); (b) Δy, the difference between the center of the spot pattern and the center of the well along the y axis of the plate (row-wise, short axis); and (c) α, the counter-clockwise angle between the long axis of the plate bottom and the long axis of the plate top of a 96-well plate. In a preferred embodiment, the plate meets or exceeds the following specifications: Δx≤0.2 mm, Δy≤0.2 mm, and α≤0.1°.

The following non-limiting examples serve to illustrate rather than limit the present invention.

Examples

Measurement of Biomarkers Indicative of Lung Cancer

Serum samples from 40 heavy smokers, 44 NSCLC patients (30 stage I/II), 20 SCLC patients, and 24 healthy controls were tested in randomized order on twelve MSD multiplex panels containing ~100 assays. Samples were tested in duplicates. Each plate contained eight calibrators in triplicates and QC samples. In general, the assay format was as follows, with minor alterations for specific assay panels as indicated in the assay protocols provided with each assay kit (supplied by Meso Scale Discovery, Rockville, Md.): (1) block MSD MULTI-SPOT® plate for 1 hour with appropriate MSD® blocking solution and wash; (2) add 25 μl assay diluent to each well, if specified; (3) add 25 μl calibrator, or sample (diluted as appropriate) to each well; (4) incubate with shaking for 1-3 hours (time as specified) and wash the well; (5) add 25 μl labeled detection antibody solution to each well; (6) incubate with shaking for 1-2 hours (time as specified) and wash the well; (7) add 150 μl MSD read buffer to each well; (8) read plate immediately on MSD SECTOR® 6000 Reader (supplied by Meso Scale Discovery, Rockville, Md.). Most sample concentrations were within the reportable range: all samples for more than half of the assays, and more than 90% of samples for another quarter of assays. There were only seven assays for which a significant number of sample concentrations were close to or below the detection limits.

ROC analysis was performed for discrimination between several classes, such as healthy and smoker versus cancer; smoker versus NSCLC; smoker versus SCLC, and smokers versus NSCLC (stage I/II only). Assays were ranked by the "area under the curve" (auc) of the ROC analysis. In addition, the ability of assays to separate disease classes was investigated visually using scatter plots. The results are shown in Table 3.

TABLE 3

The top 40 of approximately 100 biomarkers based on ROC area analysis.

| Normal + Smoker vs SCLC + NSCLC | | Smoker vs NSCLC | | Smoker vs SCLC | |
| --- | --- | --- | --- | --- | --- |
| Assay | ROC area | Assay | ROC area | Assay | ROC area |
| NME-2 | 0.92 | ENA-78 | 0.92 | KGF | 0.94 |
| KGF | 0.89 | hMDC | 0.90 | hMDC | 0.91 |
| PIGF | 0.88 | NME-2 | 0.89 | ENA-78 | 0.90 |
| hMDC | 0.87 | KGF | 0.89 | OPG | 0.89 |
| HGF | 0.85 | PIGF | 0.86 | NME-2 | 0.89 |
| ITAC | 0.85 | RANTES | 0.86 | GCLM-3 | 0.85 |
| OPG | 0.83 | Flt-3L | 0.82 | ITAC | 0.85 |
| hMCP1 (9) | 0.83 | HGF | 0.80 | Adiponectin | 0.85 |
| GPI-1 | 0.82 | hMCP1 (9) | 0.80 | MMP-3 | 0.83 |
| MCP-1 (GN) | 0.81 | SAT-3 | 0.80 | AKR1C2-1 | 0.82 |
| TNF RII | 0.81 | MIP-1-b | 0.79 | SAT-3 | 0.81 |
| Flt-3L | 0.80 | OPG | 0.78 | GPI-1 | 0.81 |
| MMP-3 | 0.77 | GCLM-3 | 0.78 | PIGF | 0.80 |
| Adiponectin | 0.76 | MCP-1 (GN) | 0.78 | PPP2R4-3 | 0.79 |
| SAT-3 | 0.76 | TNF RII | 0.78 | TNF RII | 0.79 |
| MIP-1a (cust) | 0.75 | VEGF-D | 0.77 | MIG | 0.78 |
| IL-6 | 0.75 | ITAC | 0.76 | MIP-1-b | 0.78 |
| VEGF-D | 0.74 | MMP-10 | 0.76 | RANTES | 0.76 |
| GCLM-3 | 0.73 | GPI-1 | 0.75 | EPO | 0.76 |
| TPO | 0.73 | PPP2R4-3 | 0.74 | FABP-2 | 0.75 |
| TIMP-1 | 0.72 | AKR1B1-2 | 0.74 | IL-15 | 0.75 |
| IL-16 | 0.72 | PAI-1 | 0.74 | hMIP-1b | 0.75 |
| PPP2R4-3 | 0.71 | Amy1A | 0.73 | G-CSF | 0.75 |
| TNF RI | 0.71 | hMIP-1b | 0.73 | MIP-1a (cust) | 0.74 |
| sFas | 0.71 | P-Cadherin | 0.73 | IL-16 | 0.74 |
| S100A6-3 | 0.71 | hTARC | 0.71 | HGF | 0.74 |
| IL-5 | 0.71 | IL-4 | 0.70 | IL-6R | 0.73 |
| ENA-78 | 0.71 | EPO | 0.70 | sFas | 0.72 |
| EPO | 0.70 | MIP-1a (cust) | 0.69 | hMCP1 (9) | 0.71 |
| P-Cadherin | 0.70 | MMP-1 | 0.69 | EGF | 0.71 |
| IL-4 | 0.70 | IL-6 | 0.69 | Flt-3L | 0.70 |
| VEGF | 0.69 | IL-5 | 0.68 | IL-6 | 0.70 |
| FABP-2 | 0.68 | sFas | 0.68 | SFN-5 | 0.69 |
| Thrombomodulin | 0.68 | MIG | 0.68 | VEGF-C | 0.69 |
| IL-7 | 0.68 | FABP-2 | 0.68 | VCAM-1 | 0.69 |
| Amy1A | 0.67 | Adiponectin | 0.68 | S100A6-3 | 0.69 |
| BPI | 0.67 | hMCP-4 | 0.67 | PAI-1 | 0.69 |
| IFN-g | 0.66 | Prolactin | 0.67 | hTARC | 0.69 |
| MMP-10 | 0.66 | FGF | 0.66 | Thrombomodulin | 0.69 |
| bFGF | 0.65 | MMP-3 | 0.66 | MCP-1 (GN) | 0.69 |

A correlation analysis of selected biomarkers tested was performed and the results are shown in Table 4 (FIG. 1).

In a training set of 300 samples, 12 serum and 6 plasma markers had areas under an ROC curve (ROC areas) of 0.7 or higher. A logistic regression model with 100× cross-validation was used to develop a multi-marker panel. Table 5a shows a selection of serum biomarker panels. Several panels with only four markers showed ROC areas of 0.95. Adding additional markers increased the ROC area only marginally. Table 5b shows a selection of plasma panels. In contrast to serum, the ROC area increased for panels with an increasing number of assays up to 8 markers. Since there was only marginal improvement between 6-marker panels and 8-marker panels, a 6-marker panel was selected as primary panel. One serum panel (Flt-3L, EGFR, MMP-3, and NME-2) and one plasma panel (Flt-3L, cytokeratin-19, MMP-3, Flt-1, KGF, and PlGF) were selected and tested using approximately 250 additional samples from the same cohort. For the serum panel, the ROC area dropped to 0.85 (vs. 0.95 for the training set); for the plasma panel, the ROC area dropped to 0.81 (vs. 0.93). Nevertheless, even the ROC area of 0.85 for the serum panel with clinical sensitivity and specificity of 81% and 84%, respectively, and the ROC area of 0.81 for the plasma panel with clinical sensitivity and specificity of 76% and 78%, respectively, is clinically useful.

Analysis of the combined training and test sets with 100× cross-validation resulted in a 4-marker serum panel (Flt-3L, EGFR, MMP-3, and NME-2) with an ROC area of 0.91 and clinical sensitivity and specificity of 88% and 82%, respectively, and a 5-marker plasma panel (Flt-3L, cytokeratin-19, Flt-1, KGF, and HGF) with an ROC area of 0.91 and clinical sensitivity and specificity of 84% and 83%, respectively.

TABLE 5a

Serum Panels.

| Panel (Serum; Training Set with Cross-validation) | # Markers | AUC | AUC C.I Low | AUC C.I. High | Mean (% Correct) | Std. Dev. (% Correct) | Specificity | Sensitivity |
| --- | --- | --- | --- | --- | --- | --- | --- | --- |
| Flt_3L | 1 | 0.852 | 0.843 | 0.862 | 78 | 5 | 85% | 73% |
| EGFR | 1 | 0.822 | 0.813 | 0.832 | 75 | 5 | 72% | 80% |
| MMP_2 | 1 | 0.820 | 0.810 | 0.830 | 77 | 5 | 80% | 75% |
| MMP_3 | 1 | 0.813 | 0.804 | 0.823 | 75 | 5 | 89% | 65% |
| NME_2 | 1 | 0.775 | 0.764 | 0.786 | 74 | 6 | 68% | 81% |
| Osteopontin | 1 | 0.655 | 0.643 | 0.668 | 64 | 6 | 61% | 67% |
| Flt_3L + NME_2 | 2 | 0.903 | 0.895 | 0.910 | 84 | 4 | 81% | 90% |
| Flt_3L + MMP_3 | 2 | 0.901 | 0.893 | 0.909 | 85 | 4 | 85% | 86% |
| EGFR + MMP_3 | 2 | 0.901 | 0.894 | 0.907 | 82 | 4 | 78% | 87% |
| Flt_3L + EGFR | 2 | 0.887 | 0.879 | 0.894 | 81 | 5 | 76% | 88% |
| MMP_3 + NME_2 | 2 | 0.886 | 0.878 | 0.893 | 81 | 5 | 86% | 77% |
| MMP_3 + Osteopontin | 2 | 0.882 | 0.874 | 0.889 | 79 | 5 | 73% | 89% |
| Flt_3L + MMP_3 + NME_2 | 3 | 0.938 | 0.932 | 0.944 | 89 | 4 | 86% | 92% |
| Flt_3L + MMP_3 + GPI | 3 | 0.929 | 0.922 | 0.936 | 88 | 5 | 84% | 94% |
| EGFR + MMP_3 + NME_2 | 3 | 0.928 | 0.921 | 0.934 | 87 | 4 | 85% | 89% |
| Flt_3L + MMP_3 + Osteopontin | 3 | 0.926 | 0.920 | 0.933 | 87 | 4 | 86% | 88% |
| Flt_3L + MMP_3 + NME_2 + Osteopontin | 4 | 0.954 | 0.950 | 0.958 | 89 | 4 | 87% | 93% |
| Flt_3L + MMP_3 + NME_2 + IL2_R | 4 | 0.953 | 0.949 | 0.958 | 91 | 4 | 91% | 91% |
| Flt_3L + EGFR + MMP_3 + NME_2 | 4 | 0.945 | 0.939 | 0.950 | 88 | 4 | 85% | 95% |
| Flt_3L + MMP_3 + NME_2 + Osteopontin + GPI | 5 | 0.958 | 0.951 | 0.965 | 91 | 4 | 87% | 95% |
| Flt_3L + MMP_3 + S100A6 + Osteopontin + GPI | 5 | 0.957 | 0.952 | 0.962 | 90 | 4 | 85% | 97% |
| Flt_3L + MMP_3 + NME_2 + Osteopontin + IL2_R | 5 | 0.957 | 0.953 | 0.961 | 90 | 4 | 88% | 94% |
| MMP_2 + MMP_3 + NME_2 + Osteopontin + GPI | 5 | 0.946 | 0.940 | 0.951 | 90 | 4 | 89% | 90% |
| Flt_3L + MMP_2 + MMP_3 + NME_2 + Osteopontin | 5 | 0.943 | 0.937 | 0.949 | 89 | 4 | 85% | 94% |

Column 1 shows the selected panels comprised of 1 up to 5 markers.
Column 3 shows the ROC area, and columns 4 & 5 upper and lower confidence interval of the ROC area based on 100-fold cross-validation.
Columns 6 and 7 show the percentage of samples correctly predicted by the panel and the error of the prediction (estimated from the cross-validation).
Columns 8 and 9 show the clinical sensitivity and clinical specificity at the optimum point of the ROC area (using the assumption that the cost of false positives and false negatives are equivalent).

TABLE 5b

Plasma Panels

| Panel (EDTA-Plasma; Training Set with Cross-validation) | # Markers | AUC | AUC C.I Low | AUC C.I. High | Mean (% Correct) | Std. Dev. (% Correct) | Specificity | Sensitivity |
| --- | --- | --- | --- | --- | --- | --- | --- | --- |
| Flt_3L | 1 | 0.794 | 0.784 | 0.805 | 73 | 6 | 80% | 69% |
| CytoKeratin_19 | 1 | 0.785 | 0.775 | 0.795 | 70 | 5 | 85% | 62% |
| EGFR | 1 | 0.742 | 0.732 | 0.752 | 65 | 5 | 86% | 51% |
| MMP_3 | 1 | 0.726 | 0.715 | 0.738 | 64 | 6 | 60% | 80% |
| Flt_1 | 1 | 0.679 | 0.668 | 0.690 | 62 | 5 | 84% | 45% |
| KGF | 1 | 0.630 | 0.617 | 0.644 | 60 | 6 | 69% | 55% |
| PlGF | 1 | 0.508 | 0.492 | 0.524 | 53 | 7 | 56% | 50% |
| Flt_3L + CytoKeratin_19 | 2 | 0.861 | 0.853 | 0.870 | 80 | 5 | 83% | 77% |
| CytoKeratin_19 + MMP_3 | 2 | 0.859 | 0.851 | 0.867 | 81 | 5 | 85% | 77% |
| Flt_3L + Flt_1 | 2 | 0.831 | 0.821 | 0.841 | 75 | 6 | 92% | 60% |
| CytoKeratin_19 + KGF | 2 | 0.827 | 0.818 | 0.836 | 75 | 5 | 71% | 84% |
| CytoKeratin_19 + PlGF | 2 | 0.823 | 0.813 | 0.833 | 76 | 5 | 86% | 66% |
| Flt_3L + MMP_3 | 2 | 0.819 | 0.810 | 0.828 | 74 | 5 | 68% | 81% |
| CytoKeratin_19 + Flt_1 + KGF | 3 | 0.886 | 0.878 | 0.894 | 84 | 5 | 87% | 80% |

TABLE 5b-continued

Plasma Panels

| Panel (EDTA-Plasma; Training Set with Cross-validation) | # Markers | AUC | AUC C.I Low | AUC C.I. High | Mean (% Correct) | Std. Dev. (% Correct) | Specificity | Sensitivity |
|---|---|---|---|---|---|---|---|---|
| Flt_3L + CytoKeratin_19 + MMP_3 | 3 | 0.885 | 0.877 | 0.893 | 83 | 5 | 90% | 77% |
| CytoKeratin_19 + Flt_1 + PlGF | 3 | 0.880 | 0.872 | 0.889 | 82 | 5 | 86% | 79% |
| CytoKeratin_19 + MMP_3 + KGF | 3 | 0.868 | 0.860 | 0.876 | 82 | 4 | 90% | 75% |
| CytoKeratin_19 + MMP_3 + PlGF | 3 | 0.867 | 0.858 | 0.875 | 83 | 5 | 85% | 80% |
| Flt_3L + CytoKeratin_19 + KGF | 3 | 0.865 | 0.856 | 0.874 | 81 | 5 | 81% | 83% |
| CytoKeratin_19 + MMP_3 + Flt_1 | 3 | 0.864 | 0.856 | 0.872 | 81 | 4 | 85% | 77% |
| CytoKeratin_19 + MMP_3 + Flt_1 + PlGF | 4 | 0.911 | 0.903 | 0.919 | 86 | 5 | 90% | 82% |
| CytoKeratin_19 + Flt_1 + KGF + PlGF | 4 | 0.911 | 0.904 | 0.918 | 86 | 4 | 90% | 82% |
| Flt_3L + CytoKeratin_19 + Flt_1 + PlGF | 4 | 0.909 | 0.901 | 0.917 | 84 | 5 | 91% | 78% |
| CytoKeratin_19 + MMP_3 + Flt_1 + KGF | 4 | 0.903 | 0.895 | 0.910 | 85 | 4 | 95% | 78% |
| Flt_3L + CytoKeratin_19 + Flt_1 + KGF | 4 | 0.901 | 0.893 | 0.909 | 86 | 5 | 87% | 85% |
| CytoKeratin_19 + EGFR + MMP_3 + PlGF | 4 | 0.899 | 0.893 | 0.906 | 84 | 4 | 88% | 80% |
| Flt_3L + CytoKeratin_19 + MMP_3 + CEA | 4 | 0.897 | 0.889 | 0.905 | 85 | 5 | 90% | 80% |
| Flt_3L + CytoKeratin_19 + MMP_3 + IL2_R | 4 | 0.896 | 0.888 | 0.904 | 84 | 5 | 89% | 80% |
| Flt_3L + CytoKeratin_19 + MMP_3 + PlGF | 4 | 0.891 | 0.883 | 0.899 | 84 | 5 | 90% | 79% |
| Flt_3L + CytoKeratin_19 + MMP_3 + Flt_1 | 4 | 0.890 | 0.882 | 0.898 | 84 | 5 | 91% | 78% |
| Flt_3L + CytoKeratin_19 + EGFT + MMP_3 | 4 | 0.889 | 0.882 | 0.896 | 81 | 5 | 93% | 73% |
| Flt_3L + CytoKeratin_19 + MMP_3 + KGF | 4 | 0.888 | 0.880 | 0.896 | 83 | 5 | 93% | 73% |
| CytoKeratin_19 + MMP_3 + Flt_1 + KGF + PlGF | 5 | 0.924 | 0.917 | 0.930 | 87 | 5 | 93% | 82% |
| CytoKeratin_19 + EGFR + MMP_3 + Flt_1 + PlGF | 5 | 0.923 | 0.918 | 0.929 | 86 | 4 | 92% | 82% |
| Flt_3L + CytoKeratin_19 + Flt_1 KGF + PlGF | 5 | 0.923 | 0.916 | 0.930 | 88 | 4 | 89% | 87% |
| Flt_3L + CytoKeratin_19 + MMP_3 + Flt_1 + PlGF | 5 | 0.920 | 0.913 | 0.927 | 86 | 5 | 88% | 84% |
| Flt_3L + CytoKeratin_19 + MMP_3 + Flt_1 + KGF | 5 | 0.911 | 0.903 | 0.918 | 86 | 4 | 96% | 79% |
| CytoKeratin_19 + MMP_3 + Flt_1 + KGF + IL2_R + PlGF | 6 | 0.939 | 0.934 | 0.945 | 89 | 4 | 91% | 87% |
| CytoKeratin_19 + EGFR + MMP_3 + Flt_1 + IL2_R + PlGF | 6 | 0.935 | 0.929 | 0.941 | 89 | 4 | 93% | 85% |
| CytoKeratin_19 + EGFR + MMP_3 + Flt_1 + B7_H3 + PlGF | 6 | 0.934 | 0.928 | 0.939 | 86 | 4 | 90% | 83% |
| EGFR + MMP_3 + Flt_1 + CEA + IL2_R + PlGF | 6 | 0.933 | 0.927 | 0.938 | 87 | 4 | 84% | 90% |
| CytoKeratin_19 + MMP_3 + Flt_1 + Cytokeratin_8 + KGF + PlGF | 6 | 0.932 | 0.926 | 0.938 | 89 | 4 | 89% | 89% |
| CytoKeratin_19 + MMP_3 + Flt_1 + KGF + B7_H3 + PlGF | 6 | 0.930 | 0.925 | 0.936 | 86 | 5 | 91% | 82% |
| CytoKeratin_19 + EGFR + MMP_3 + Flt_1 + Cytokeratin_8 + PlGF | 6 | 0.930 | 0.924 | 0.936 | 88 | 4 | 89% | 88% |
| Flt_3L + CytoKeratin_19 + Flt_1 + CEA + KGF + PlGF | 6 | 0.930 | 0.923 | 0.936 | 88 | 4 | 92% | 84% |
| Flt_3L + CytoKeratin_19 + MMP_3 + Flt_1 + KGF + PlGF | 6 | 0.929 | 0.923 | 0.935 | 88 | 4 | 94% | 83% |
| Flt_3L + EGFR + MMP_3 + Flt_1 + IL2_R + PlGF | 6 | 0.925 | 0.919 | 0.931 | 84 | 5 | 96% | 79% |
| CytoKeratin_19 + EGFR + Flt_1 + CEA + KGF + IL2_R + PlGF | 7 | 0.946 | 0 940 | 0.951 | 89 | 4 | 91% | 88% |
| EGFR + MMP_3 + Flt_1 + CEA + KGF + IL2_R + PlGF | 7 | 0.944 | 0.939 | 0.949 | 88 | 4 | 93% | 85% |
| CytoKeratin_19 + EGFR + MMP_3 + Flt_1 + KGF + IL2_R + PlGF | 7 | 0.943 | 0.937 | 0.949 | 89 | 4 | 93% | 86% |
| CytoKeratin_19 + EGFR + MMP_3 + Flt_1 + KGF + B7_H3 + PlGF | 7 | 0.941 | 0.936 | 0.947 | 87 | 4 | 90% | 84% |
| Flt_3L + CytoKeratin_19 + MMP_3 + Flt_1 + KGF + IL2_R + PlGF | 7 | 0.941 | 0.935 | 0.947 | 89 | 4 | 93% | 86% |
| CytoKeratin_19 + EGFR + MMP_3 + Flt_1 + KGF + IL2_R + B7_H3 + PlGF | 8 | 0.947 | 0.941 | 0.953 | 88 | 4 | 89% | 87% |
| CytoKeratin_19 + EGFR + MMP_3 + Flt_1 + CEA + KGF + IL2_R + PlGF | 8 | 0.946 | 0.940 | 0.951 | 91 | 4 | 94% | 89% |
| Flt_3L + CytoKeratin_19 + EGFR + Flt_1 + CEA + KGF + IL2_R + PlGF | 8 | 0.945 | 0.940 | 0.951 | 89 | 4 | 94% | 86% |
| Flt_3L + CytoKeratin_19 + EGFR + Flt_1 + CEA + KGF + IL2_R + MCP_1 + PlGF | 9 | 0.942 | 0.937 | 0.948 | 89 | 4 | 89% | 89% |
| Flt_3L + CytoKeratin_19 + EGFR + Flt_1 + CEA + KGF + HGF + IL2_R + PlGF | 9 | 0.942 | 0.937 | 0.948 | 89 | 4 | 93% | 87% |

Several markers were found to have clinical sensitivity and specificity exceeding 70% and 80%. Table 6 shows sensitivity and specificity for a set of markers from this study.

TABLE 6

ROC "area under the curve", Clinical Sensitivity and Clinical Specificity for selected markers for diagnosis of NSCLC in heavy smokers.

| Assay | ROC area | Sensitivity | Specificity |
|---|---|---|---|
| MDC | 0.90 | 88% | 84% |
| NME-2 | 0.89 | 88% | 84% |
| KGF | 0.89 | 93% | 82% |
| PlGF | 0.86 | 80% | 82% |
| Flt-3L | 0.82 | 78% | 77% |
| HGF | 0.80 | 83% | 73% |
| MCP1 | 0.80 | 83% | 66% |
| SAT-1 | 0.80 | 78% | 77% |
| MIP-1-b | 0.79 | 73% | 77% |
| GCLM | 0.78 | 85% | 77% |
| OPG | 0.78 | 75% | 75% |
| TNF RII | 0.78 | 65% | 86% |
| VEGF-D | 0.77 | 65% | 77% |
| ITAC | 0.76 | 73% | 68% |
| MMP-10 | 0.76 | 83% | 64% |
| GPI | 0.75 | 75% | 61% |
| PPP2R4 | 0.74 | 73% | 84% |
| AKR1B1 | 0.74 | 85% | 68% |
| Amy1A | 0.73 | 70% | 71% |
| MIP-1b | 0.73 | 80% | 68% |
| P-Cadherin | 0.73 | 73% | 68% |
| EPO | 0.70 | 68% | 68% |

MMP-3 and Adiponectin are two markers with a high ROC area for diagnosis of SCLC. Additional markers can be used as a part of a multimarker panel, including but not limited to IP-10, TPO, EPO, sFlt-1, S100A6 and IL-6; the concentrations of these markers were significantly higher (or lower) for a subset of cancer patients.

Logistic regression was used to model various combinations of biomarkers. Briefly, for each sample matrix, random subsampling with cross-validation was used to calculate ROC and AUC. Table 7 shows the results of this analysis after log transformation. Table 7(a) shows the results for plasma biomarkers and 7(b) shows the results for serum biomarkers.

TABLE 7(a)

Results for Plasma Biomarkers

| Marker | AUC | C.I. Lower | C.I. Upper |
|---|---|---|---|
| Flt_3L | 0.729 | 0.726 | 0.732 |
| NSE | 0.712 | 0.709 | 0.715 |
| CytoKeratin_19 | 0.700 | 0.696 | 0.703 |
| NME_2 | 0.691 | 0.688 | 0.695 |
| EGFR | 0.661 | 0.658 | 0.664 |
| cKit | 0.658 | 0.655 | 0.662 |
| GPI | 0.656 | 0.653 | 0.660 |
| MMP_3 | 0.643 | 0.640 | 0.647 |
| S100A6 | 0.633 | 0.629 | 0.637 |
| Cytokeratin_8 | 0.621 | 0.617 | 0.625 |
| Flt_1 | 0.619 | 0.616 | 0.623 |
| HGF | 0.617 | 0.613 | 0.620 |
| IL2_R | 0.613 | 0.609 | 0.617 |
| MMP_9 | 0.612 | 0.608 | 0.616 |
| ErbB2 | 0.609 | 0.606 | 0.613 |
| CEA | 0.606 | 0.603 | 0.610 |
| KGF | 0.598 | 0.594 | 0.601 |
| cMET | 0.591 | 0.587 | 0.595 |
| IL_6 | 0.590 | 0.587 | 0.594 |

TABLE 7(a)-continued

Results for Plasma Biomarkers

| Marker | AUC | C.I. Lower | C.I. Upper |
|---|---|---|---|
| Osteopontin | 0.578 | 0.574 | 0.582 |
| MMP_2 | 0.561 | 0.557 | 0.565 |
| I_TAC | 0.546 | 0.542 | 0.550 |
| Ca19_9 | 0.541 | 0.536 | 0.545 |
| B7_H3 | 0.539 | 0.536 | 0.542 |
| Mesothelin | 0.539 | 0.536 | 0.542 |
| uPA | 0.538 | 0.535 | 0.541 |
| VEGF | 0.537 | 0.533 | 0.540 |
| MDC | 0.536 | 0.533 | 0.540 |
| TNFR_2 | 0.536 | 0.533 | 0.540 |
| OPG | 0.534 | 0.531 | 0.537 |
| M_CSF | 0.531 | 0.528 | 0.534 |
| MCP_1 | 0.531 | 0.526 | 0.535 |
| SAA | 0.528 | 0.524 | 0.532 |

TABLE 7(b)

Results for Serum Biomarkers

| Marker | AUC | C.I. Lower | C.I. Upper |
|---|---|---|---|
| Flt_3L | 0.786 | 0.783 | 0.789 |
| MMP_2 | 0.781 | 0.778 | 0.784 |
| EGFR | 0.759 | 0.756 | 0.762 |
| MMP_3 | 0.745 | 0.742 | 0.749 |
| ErbB2 | 0.734 | 0.731 | 0.737 |
| NME_2 | 0.729 | 0.725 | 0.732 |
| CytoKeratin_19 | 0.684 | 0.681 | 0.688 |
| Dkk_1 | 0.670 | 0.667 | 0.674 |
| E_Cadherin | 0.669 | 0.665 | 0.672 |
| VEGF_D | 0.663 | 0.659 | 0.666 |
| cMET | 0.646 | 0.642 | 0.649 |
| MDC | 0.642 | 0.638 | 0.646 |
| cKit | 0.640 | 0.637 | 0.644 |
| Osteopontin | 0.639 | 0.635 | 0.642 |
| IL_6 | 0.637 | 0.633 | 0.640 |
| SCF | 0.630 | 0.627 | 0.634 |
| AFP | 0.626 | 0.622 | 0.629 |
| uPA | 0.619 | 0.615 | 0.622 |
| S100A6 | 0.613 | 0.609 | 0.616 |
| CA15_3 | 0.611 | 0.607 | 0.614 |
| MMP_9 | 0.605 | 0.601 | 0.609 |
| B7_H3 | 0.597 | 0.593 | 0.600 |
| NSE | 0.596 | 0.593 | 0.600 |
| Nectin_4 | 0.596 | 0.592 | 0.599 |
| Adiponectin | 0.596 | 0.592 | 0.599 |
| OPG | 0.592 | 0.588 | 0.596 |
| KGF | 0.591 | 0.588 | 0.595 |
| CEA | 0.578 | 0.574 | 0.581 |
| Mesothelin | 0.567 | 0.564 | 0.571 |
| MCP_1 | 0.564 | 0.559 | 0.568 |
| SAA | 0.560 | 0.556 | 0.563 |
| PLGF | 0.552 | 0.548 | 0.556 |
| GPI | 0.548 | 0.545 | 0.551 |

Various publications and test methods are cited herein, the disclosures of which are incorporated herein by reference in their entireties, In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

What is claimed is:

1. A method for evaluating the efficacy of a first treatment regimen in a patient diagnosed with small cell lung cancer (SCLC) and undergoing the treatment regimen, said method comprising:

(a) administering a first treatment regimen to said patient wherein said first treatment regimen is administration of one or more of cisplatin, carboplatin, irinotecan and etoposide;
(b) receiving a comparison of a normal control level of biomarkers versus a level of biomarkers in a test sample obtained from said patient undergoing said first treatment regimen for SCLC, wherein said biomarkers are MMP-3 and/or Adiponectin in combination with at least one biomarker selected from the group consisting of IP-10, TPO, EPO, sFlt-1, S100A6 and IL-6;
(c) evaluating from said comparison whether said patient is responsive to said first treatment regimen;
(d) identifying the patient as being responsive to said first treatment regimen or not responsive to said first treatment regimen, and performing one of (e) or (f):
(e) administering a second treatment regimen if the patient is not responsive to said first treatment regimen, wherein said second treatment regimen is different from the first treatment regimen, and is administration of one or more of cisplatin, carboplatin, irinotecan and etoposide, or
(f) continuing administration of said first treatment regimen if the patient is responsive to said first treatment regimen.

2. The method of claim 1 wherein said comparison comprises receiving results of a multiplexed assay of a plurality of said biomarkers in said test sample, wherein said multiplexed assay is conducted using one reaction volume comprising said test sample.

3. The method of claim 2 wherein said assay is conducted in an assay chamber wherein the assay chamber is a well of an assay plate.

4. The method of claim 3 wherein said assay chamber is a cartridge.

5. The method of claim 1 wherein said test sample is selected from the group consisting of blood, peripheral blood mononuclear cells (PBMC), isolated blood cells, urine, serum, and plasma.

6. The method of claim 1 wherein said test sample is serum or plasma.

7. The method of claim 1 wherein said test sample is serum.

8. The method of claim 1 wherein said sample is plasma.

9. The method of claim 1 wherein said levels are compared using an immunoassay.

10. The method of claim 1, wherein the comparison is conducted with one or more vials, containers, or compartments, containing a set of calibrator proteins.

11. The method of claim 1, wherein the comparison comprises at least four discrete binding domains, which are in the form of a spot pattern.

12. The method of claim 1, further comprising at least one of:
(i) increasing or decreasing a dosage, frequency, or route of administration of a therapeutic agent of the treatment regimen;
(ii) adding an additional therapeutic agent and/or palliative agent to the treatment regimen;
(iii) if the therapeutic regimen comprises the administration of two or more therapeutic and/or palliative agents, modifying the treatment regimen to eliminate one or more of the therapeutic and/or palliative agents.

* * * * *